United States Patent [19]

Hough

[11] 4,081,484

[45] Mar. 28, 1978

[54] METHOD FOR PREPARING CARBORANE

[75] Inventor: William Vernon Hough, Evans City, Pa.

[73] Assignee: Mine Safety Appliances Company, Pittsburgh, Pa.

[21] Appl. No.: 690,859

[22] Filed: May 28, 1976

[51] Int. Cl.$^2$ .............................................. C07F 5/02
[52] U.S. Cl. ............................................ 260/606.5 B
[58] Field of Search ................................ 260/606.5 G

[56] References Cited

U.S. PATENT DOCUMENTS 3,463,820  8/1969  Ager et al. ..................... 260/606.5 B
3,505,409  4/1970  Bobinski et al. .............. 260/606.5 B

OTHER PUBLICATIONS

Heying et al., Inorg. Chem. 2, pp. 1089-1092 (1963).
Hill et al., Inorg. Chem. 14, pp. 1244-1249 (1975).
Fein et al., Inorg. Chem. 2, pp. 1111-1119 (1963).
Chemical Abstracts, 80, 37268w (1974).

*Primary Examiner*—Helen M. S. Sneed

[57] ABSTRACT

Improved yields of n-hexyl carborane are obtained by slowly adding an ether solution of decaborane and dialkylsulfide to 1-octyne at a temperature between about 110° and 140° C.

5 Claims, No Drawings

METHOD FOR PREPARING CARBORANE

FIELD OF THE INVENTION

This invention relates to an improved method for preparing 1-n-hexyl-1,2 dicarba(closo)-dodecaborane(12), commonly called and hereinafter referred to as n-hexyl carborane.

BACKGROUND OF THE INVENTION

Carboranes are useful as burning rate modifiers in solid propellant grains, n-hexyl carborane being particularly useful and preferred because it is a liquid having a melting point of about $-50°$. Heretofore carboranes have been prepared by reaction of acetylenic compounds with diligand derivatives of decaborane, $B_{10}H_{12}L_2$, (L=Lewis base) or solutions of decaborane and a Lewis base which react as the diligand derivatives. Acetonitrile and lower dialkylsulfides are representative of appropriate Lewis bases, and, when forming n-hexyl carborane, the acetylenic compound used in 1-octyne. These prior preparations of alkyl carboranes are characterized by low yields of about 30 percent. Heying et al, A New Series of Organoboranes, I, Carboranes from the Reaction of Decaborane with Acetylenic Compounds. *Inorganic Chemistry*, Vol. 2, p 1089 (1963); Fein, et al, Carboranes II, The Preparation of 1- and 1,2-Substituted Carboranes, ibid, Vol. 2, p 1115 (1963), Hill, et al, Kenetics and Mechanism of Carborane Formation, ibid, Vol. 14, p 1244 (1975). Hill, et al report (at p 1246) that yields of carboranes were independent of temperature over the range of 38°–100° C for octyne. Temperatures in excess of about 100° C have not been used in prior art reactions because the reactant decaborane derivative solutions decompose or degrade. Low yields are a substantial economic consideration as starting materials are expensive, decaborane, for example, is currently priced in quantity at about $800 per pound, and the product recovery and purification steps are tedious and expensive.

SUMMARY OF THE INVENTION

It is the object of this invention to provide an improved method of making n-hexyl carborane. This invention is based on my discovery that substantially increased yields of n-hexyl carborane are obtained from the reaction of 1-octyne with an ether solution of decaborane and dialkylsulfide when the reaction temperature is maintained above about 110° C and below about 140° C and the decaborane solution, maintained at a temperature below that at which it decomposes, is slowly added to 1-octyne maintained at the desired reaction temperature, the rate of addition being commensurate with the rate of formation of n-hexyl carborane.

DESCRIPTION OF THE INVENTION

The following example is illustrative of the best mode now contemplated for carrying out the invention.

Decaborane (117.4 g.) was mixed with 250 ml of n-butyl ether, 91 ml of dioxane and 170 ml of di-n-butyl sulfide until the decaborane dissolved. The solution stood at ambient room temperature overnight, during which time 0.1 to 0.4 mol of hydrogen is evolved from reaction of the sulfide with a small portion of the decaborane which is believed to form bis-(di-n-butyl sulfide)-decaborane according to:

$$B_{10}H_{14} + S(C_4H_9)_2 \rightarrow B_{10}H_{12}S(C_4H_9)_2 + H_2$$

Octyne (285 ml) and 285 ml of n-butyl ether were charged to a two liter flask equipped with a thermometer, stirrer, reflux condenser, and addition funnel. The previously prepared decaborane solution was charged to the funnel. The octyne-ether solution was heated to reflux (130.5° C, 738 mm) and when good refluxing was achieved the decaborane solution was added dropwise over a period of 3¼ hours. The temperature of the flask contents varied from 129° C to 131° C, the substantially constant temperature being maintained by refluxing the reactive mixture. Hydrogen evolution commenced immediately on addition of the decaborane solution, indicating commencement of the reaction forming n-hexyl carborane:

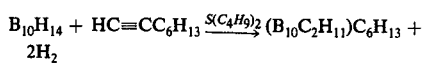

The reaction was substantially complete when the solution addition was completed, as evidenced by the hydrogen evolution of 31.5 liters. Only 1.1 liters of hydrogen was evolved during subsequent refluxing of the reaction mixture for one hour.

The n-hexyl carborane is separated by conventional means from the solvents and sulfide-decaborane by-products. The product solution was cooled to room temperature and the solvent ether was stripped under vacuum, while gradually raising the temperature to 162° C. The pot liquor was cooled and pyridine was added to render the by-products insoluble in hydrocarbons. The resultant viscous fluid was extracted four times with n-pentane and the combined extracts were washed with 8% aqueous NaOH solution and a 5% aqueous NaCl solution. Pentane was distilled from the washed extract and resultant n-hexyl carborane was purified by vacuum evaporation, discarding a 29 g. forecut at a head temperature of 131° C (pot-140°). The 131.2 g. of purified n-hexyl carborane recovered was a yield of 60% of 99% purity determined by chromatographic methods.

It is preferred to use an ether solution containing about equimolar proportions of dialkylsulfide and decaborane. Although these solutions can be used immediately, if they are allowed to stand overnight, or even several days, the resultant yields are a few percent higher than when using fresh solutions. Smaller amounts of dialkylsulfide, for example, as little as 0.1 mol per mol of decaborane can be used at the expense of a slower reaction rate and somewhat diminished yield. The use of dialkylsulfides in larger proportions than equimolar with decaborane does not improve yield or reaction rate, but is not detrimental.

It is generally preferred to use an amount of 1-octyne in excess of stoichiometric to insure more rapid substantially complete reaction of decaborane, the more expensive reactant.

The highest yield is obtained when using n-dibutyl sulfide, although other sulfides may be used with some sacrifice of yield or economy. For example, yields in the range of 45–50% are obtained when using a sulfide having alkyl groups with 1,2 or 3 carbon atoms, compared to a yield of 55% to 60%, or even higher, when using n-dibutyl sulfide. Sulfides having alkyl groups with 5 or more carbon atoms are useable, but they are expensive and not readily available.

A reaction temperature of 110° or 140° is suitable, with a temperature of about 130° C preferred; at temperatures below about 110°, the yield is substantially the same as that obtainable from prior art methods; at about 140° C and higher temperatures the product carborane itself degrades or decomposes, substantially reducing the yields. The improved yields are obtainable at these temperatures only if thermal degradation of the reactant decaborane-dialkyl sulfide solution is prevented by maintaining the solution at a temperature below which it will not degrade, most conveniently ambient temperature, and slowly adding the solution to the reaction mixture at a rate commensurate with the rate of n-hexyl carborane formation. Suitably, the decaborane reactant is added over a period of about 2–3½ hours, and the rate of addition can be monitored and adjusted in accordance with the rate hydrogen is evolved from the reaction mixture.

While the preferred specific embodiment has been described in detail, this has been done by way of illustration and it will be evident to those skilled in the art that reactions can be made without departing from the scope of the invention.

I claim:

1. A method of preparing n-hexyl carborane comprising the step of adding an ether solution containing decaborane and a dialkylsulfide to 1-octyne maintained at a temperature between about 110° C and 140° C, the rate of addition being commensurate with the rate of n-hexyl carborane formation.

2. A method according to claim 1 using an ether solution of dialkyl disulfide and decaborane in substantially equimolar proportions.

3. A method according to claim 1 in which the dialkylsulfide is di-n-butyl sulfide.

4. A method according to claim 1 in which 1-octyne is mixed with an ether.

5. A method according to claim 1 in which a solution of substantially equimolar proportions of di-n-butyl sulfide and decaborane in n-butyl ether and dioxane is added over a period of 2 to 3½ hours to a mixture of 1-octyne and n-butyl ether at a temperature between about 110° and 140° C.

* * * * *